United States Patent
Pimentel

(10) Patent No.: US 7,618,624 B1
(45) Date of Patent: *Nov. 17, 2009

(54) WEIGHT CONTROL USING AN ANTI-LIPASE ANTIBODY

(75) Inventor: Julio Pimentel, Buford, GA (US)

(73) Assignees: Anitox Corporation, Lawrenceville, GA (US); Julio L Pimentel, Buford, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/226,597

(22) Filed: Jan. 7, 1999

(51) Int. Cl.
*A61K 39/395* (2006.01)
*A61K 39/00* (2006.01)

(52) U.S. Cl. .................. 424/130.1; 424/9.2; 424/9.321; 424/139.1; 424/146.1; 424/152.1; 424/157.1; 424/442; 424/450

(58) Field of Classification Search ............. 424/130.1, 424/157.1, 158.1, 442, 450, 167.1, 164.1, 424/804, 9.2, 9.321, 139.1, 146.1, 163.1; 426/2, 60, 89, 140, 250, 657, 402.2, 817; 428/402.2; 514/524, 649; 530/388.2, 388.26, 530/389.1

See application file for complete search history.

(56) References Cited

U.S. PATENT DOCUMENTS

| | | | | |
|---|---|---|---|---|
| 4,863,959 A | * | 9/1989 | Bentley et al. | ............... 514/524 |
| 4,959,310 A | | 9/1990 | Brandon et al. | |
| 5,064,655 A | * | 11/1991 | Uster et al. | .................. 424/450 |
| 5,080,895 A | | 1/1992 | Tokoro | |
| 5,725,873 A | * | 3/1998 | Cook et al. | .................. 424/442 |
| 5,741,489 A | | 4/1998 | Pimentel | .................. 424/157.1 |
| 5,827,517 A | | 10/1998 | Cook | |
| 5,919,451 A | * | 7/1999 | Cook et al. | ............. 424/130.1 |
| 5,976,580 A | * | 11/1999 | Ivey et al. | ....................... 426/2 |
| 5,985,336 A | * | 11/1999 | Ivey et al. | ....................... 426/2 |
| 7,344,713 B1 | * | 3/2008 | Pimentel | .................. 424/130.1 |

FOREIGN PATENT DOCUMENTS

| | | | |
|---|---|---|---|
| DE | 0310931 | * 12/1989 | .................... 424/2 |
| DE | EP 0.310.931 | 12/1989 | |

OTHER PUBLICATIONS (1990) LeClerq et al. Metabolism of VLDL in genetically Lean or Fat Lines of Chicken, Reproduction, Nutrition, Development 30(6):705-715 *Abstract Only*.*
LeClercq et al., Metabolism of very low density lipoproteins in genetically lean or fat lines of chicken, Reproduction, Nutrition, Development, 30 (6): 701-715 (1990).*
Drent et al., Lipase inhibition: a novel concept in the treatment of obesity, International Journal of Obesity 17: 241-244 (1993).*
Ohkaru et al., Application of two monoclonal antibodies to either an immunosorbent enzyme assay or a competitive binding enzyme immunoassay for human serum pancreatic lipase, Clin. Chim. Acta, 182 (3): 295-300 (1989), Abstract Only.*
(c) 1998 Evans, M. Animal Nutrton Research No. 75, BASF Know—how and quality for feed industry, pp. 1-2.
1999 Shipp et al. "Hyperimmune spray dreid egges as a feed supplement for weanling pigs" Feed Mix 7:30, 32, 33.
Oct. 5-7 , 1999, K .F. Cardwell, "Mycotoxin Contamination in Foods—Anti-Nutritonal Facts," Improving Human Nutrition Through Agriculture: The Role of Internation Agricultural Research, International Institute of Tropical Agriculte. 08 B.P. 0932. Cotonou Bénin.
2004 I Csaky and S. Fekete, "Soybean: Feed Quality and Safety, Part 1: Biologically Active Components: A Review," Acta Veterinaria Hungarica 52 (3) pp. 299-313.
2004 I Csaky and S. Fekete, "Soybean Feed Quality and Safety, Part 2: Pathology of Soybean Feeding in Animals: A Review." Acta Veterinaria Hungarica 52 (3) pp. 315-326.
Feb. 2005, Farzana Panhwar, "Anti-nutritonal Factors in Oil Seeds as Aflatoxin in Ground Nuts,".
1990 LeClerq et al "Metabolism of VLDL in Genetically Lean or Fat Lines of Chicken," Reproduction, Nutrition, Development 30(6); 705-715 (previously cited as document U).

* cited by examiner

*Primary Examiner*—Gailene R Gabel
(74) *Attorney, Agent, or Firm*—Neifeld IP Law, PC

(57) ABSTRACT

A method for regulating the body weight of an animal by feeding it a liposome-encapsulated antibody against lipase.

14 Claims, No Drawings

WEIGHT CONTROL USING AN ANTI-LIPASE ANTIBODY

BACKGROUND OF THE INVENTION

1. Field of the Invention

A method for regulating body weight by adding to food a liposome-encapsulated immunoglobulin against lipase.

2. Background of the Invention

The bulk of dietary lipid is triacylglycerol. In the gastrointestinal tract a portion is hydrolized to fatty acids and glycerol by lipases. The present invention relates to a method for decreasing the amount of body weight normally gained after eating food by administering liposome-encapsulated immunoglobulins against lipase, including polyclonal antibodies, monoclonal antibodies and genetically engineered fragments thereof.

Lipases are commercially available. They are obtained from a variety of natural sources including the pancreas and a number of bacteria, e.g., *Candida rugosa, Chromobacterium* and species of *Pseudomonas*.

The production of anti-lipase antibodies can be accomplished by injecting animals, such as rodents or rabbits, with lipase and collecting the blood serum, which contains the antibody. However, this procedure is costly and invasive.

A general method for producing antibodies which is non-invasive and more economical is known. It has been observed that eggs contain 50-150 mg of various antibodies. When a hen is injected with a particular antigen, 10-20% of the antibody isolated from the eggs are specific to that antigen. Losch et al, J. Vet. Med. B. 33:609-619 (1986); Gassmann et al, Faseb J. 4:2528-2532 (1990). Chicken antibodies can be protected from stomach acidity and pepsin hydrolysis by encapsulating them within liposomes Shimuzu et al, Biosci. Biotech. Biochem. 57:1445-1449 (1993).

SUMMARY OF THE INVENTION

The invention provides a method for regulating the body weight of an animal by including in its food an effective amount of a liposome-encapsulated immunoglobulin against lipase. The stability of the immunoglobulin in the digestive tract is increased by encapsulating it in liposomes.

DESCRIPTION OF THE PREFERRED EMBODIMENTS

The amount of body weight an animal gains as a result of eating food can be decreased by including in its diet encapsulated antibodies produced using a lipase as the antigen. Lipases are commercially available from the Sigma company, which sells lipases obtained from *C. rugosa*, human pancreas, *M. javanicus*, porcine pancreas, *P. cepacia*, and species of *pseudomonas*.

Polyclonal antibodies can be produced in hen eggs using the following general procedure. Hens of about 17 weeks of age are injected with 0.1 to 2.0 mg of the antigen. The innoculum is prepared by dissolving the lipase in phosphate buffered saline and Freund's adjuvant. The antigen preparation is injected intramuscularly into two sites, 0.1 to 1.0 ml in each (right and left) pectoralis muscle. A second injection can be administered five to six weeks following the initial injection, using incomplete Freund's adjuvant. Hens are generally reinjected with the antigen preparation every two months or when the antibody titer is determined to be low. Antibody titer is conveniently determined by ELISA (enzyme linked immunoassay) methods. Eggs containing the specific antibody can be collected one week after the second injection. If the hens are injected with antigen three times, the average yield of anti-lipase in the eggs increases.

The antibodies can be purified according to the method of Kwan et al, J. Food Sci 56:1536-1541 (1991). Briefly, one volume of egg yolk is mixed with nine volumes of distilled water and left to sit overnight at 4° C. Then the aqueous portion is centrifuged at 4000 rpm for 10 minutes, and filtered through a cheese cloth to remove any excess fat. The liquid is frozen and freeze dried. After freeze drying, the antibody can be heat treated (1 hour at 50°-70° C.) to improve stability. Antibody activity can be determined by an ELISA, preferably after adjusting the protein concentration in the egg extract to 1 mg/ml as determined by the Bradford procedure.

The procedure for ELISA is as follows:

1. Plates are coated with 100 µl lipase solution (10 µg/ml) in carbonate buffer and incubated at 4° C. overnight prior to blocking with 1.5% bovine serum albumine for four hours at room temperature.
2. 100 µl of the 1 mg protein/ml egg extract is added to each well and the plates incubated at room temperature for 30 minutes.
3. Plates are washed with PBS-Tween 20 solution. 100 µl of 1:20,000 dilution of rabbit anti-chick IgG, conjugated to horseradish peroxidase, is added to each well. The plate is incubated at room temperature for 30 minutes. The exact enzyme-antibody conjugate concentration can be determined with a checkerboard titration.
4. Plates are washed with the PBS-Tween and 100 µl of TBM substrate is added to each well. The plates are incubated at room temperature for 15 minutes.
5. The reaction is stopped with 100 µl of 2 M sulfuric acid.
6. Plates are read at 455 nm in an ELISA plate reader.
7. Titer is determined as the inverse of the last dilution in which optical density of the immunized egg was similar to the un-immunized control (O.D. <0.100).

Spray-dried eggs containing lipase-specific antibodies can be prepared using the following spray drying parameters: inlet temperatures/outlet temperatures 140° C./170° C., blower at 50% capacity, compressor at 75% and pump at 30% capacity (Virtis Spray Dryer). In order to sterilize and improve the stability of the antibody, thereby increasing shelf life, spray dried eggs can be incubated at 60° C. for seven days.

In general, the amount of anti-lipase antibody added to the food is 25-1000 mg/kg, preferably 50-800 mg/kg. The amount of food which constitutes a maintenance diet can thereby be increased. The present invention provides decreased body weight gain per unit of food compared to when animals eat the same food without a liposome-encapsulated immunoglobulin against lipase.

Animals who's weight can be controlled include mammals, avians and any animal having a pancreas or that secrets lipase. Suitable mammals include humans, rats, feedlot animals such as pigs and cows, and household pets, such as dogs, cats, and horses. Suitable avians include chickens, turkeys, ducks, parrots and parakeets.

EXAMPLE 1

Antibodies against lipase from human pancrease (Sigma) was raised in leghorn hens as described above and harvested from their egg yolks. The lipase (2 mg; 250 units of activity per mg protein) was dissolved in 0.1 molar tris containing 0.1 molar sodium chloride and a serine protease inhibitor Sigma L-9780, then suspended in 0.2 ml phosphate buffer and emulsified with 0.2 ml of Freund's Complete adjuvant. This suspension was injected in each side of the breast. A second injection was performed two weeks later. Eggs were collected a week after the second injection.

EXAMPLE 2

Antibodies may become inactive when encountering the acidity of the stomach. This example demonstrates the encapsulation of anti-lipase antibodies by liposomes. Chicken antibodies (10 mg in 2 ml water) were encapsulated by mixing the antibody solution with 2 ml of diluted water containing 100 to 300 μmol of a mixture of egg lecithin/cholesterol liposomes, using the dehydration-rehydration method of Shimizu et al (1993) cited above. The final liposome suspension was frozen and later freeze dried. The freeze dried liposome was mixed with rabbit chow to achieve 750 mg/kg of rabbit chow, and fed daily for the length of the study.

EXAMPLE 3

This example illustrates the effect of a liposome-encapsulated immunoglobulin against lipase in rats. Twelve retired breeder Sprague Dawley rats (Harlan, Wis.) were individually caged and supplied with free access to water. They were fed a rabbit chow which was supplemented with corn oil in order to increase the fat content to 30%. Feed intake was monitored for 1 week in order to determine the amount of feed needed to maintain initial body weight. The rats were divided into two groups; one group was fed the high fat diet and the other group was fed the same diet with freeze dried liposomes containing the anti-lipase antibody of Example 1. The treated diet contained 750 mg of liposome-encapsulated antibody/kg of diet. The results after one week of treatment were as follows:

|  | Initial body weight (gr)* | One week feed intake (gr) | Final body weight (gr) | Difference in body weight | grams of feed needed to gain 1 gr of body weight |
|---|---|---|---|---|---|
| control | 316 | 132.3 | 327 | 11 | 12.0 |
| antibody | 319 | 129.4 | 326 | 7 | 18.5 |

*average of 6 rats,
gr = grams

EXAMPLE 4

Since it was observed that rats gained weight in Example 3, the same rats were used in a weight loss study where feed was restricted. The results were as follows:

|  | Initial body weight (gr) | Feed intake (gr) | Final body weight (gr) | Difference in Body weight (gr) |
|---|---|---|---|---|
| control | 327 | 102 | 319 | −8 |
| antibody | 326 | 101 | 317 | −9 |

EXAMPLE 5

This study demonstrates the effect of a liposome-encapsulated immunoglobulin against lipase fed to rats with an approximate maintenance level of feed intake. The results were as follows:

|  | Initial body weight (gr) | One week feed intake (gr) | One week body weight (gr) | Difference in body weight | gr of feed needed to gain 1 gr of body weight |
|---|---|---|---|---|---|
| control | 325 | 112 | 332 | 7 | 16 |
| antibody | 324 | 114 | 325 | 1 | 114 |

The antibody group gained much less weight than the control group while eating slightly more food.

It will be apparent to those skilled in the art that a number of modifications and variations may be made without departing from the scope of the present invention as set forth in the appended claims.

The invention claimed is:

1. A method for controlling weight in mammals comprising: feeding a mammal food containing an amount of a liposome-encapsulated anti-lipase antibody effective to decrease body weight gained per unit of food of said mammal after eating the food; thereby controlling the weight of said mammal.

2. The method of claim 1 wherein said anti-lipase antibody is an avian antibody.

3. The method of claim 2 wherein said liposome-encapsulated anti-lipase antibody is in a wet state and freeze drying said liposome-encapsulated anti-lipase antibody.

4. The method of claim 1 wherein said liposome is formed prior to said feeding.

5. The method of claim 1 wherein said food comprises dietary lipid.

6. The method of claim 1 wherein said animal food comprises 25 to 1000 mg of said liposome-encapsulated anti-lipase antibody per kilogram of food.

7. The method of claim 1 wherein said food comprises at least 25 mg of said liposome-encapsulated anti-lipase antibody per kilogram of food.

8. A composition for controlling weight in mammals, comprising: a mixture of food for a mammal and an amount of a liposome-encapsulated anti-lipase antibody effective to decrease body weight gained per unit of food of said mammal after eating the food composition; thereby controlling the weight of said mammal.

9. The composition of claim 8 which contains 25-1000 mg of said liposome-encapsulated anti-lipase antibody per kilogram of said food.

10. The composition of claim 8 wherein said anti-lipase antibody is an avian anti-lipase antibody.

11. The composition of claim 8 wherein said liposome-encapsulated anti-lipase antibody is in a wet state or a freeze dried state.

12. The composition of claim 8 wherein said food comprises dietary lipid.

13. The composition of claim 8 wherein said food comprises at least 25 mg of said liposome-encapsulated anti-lipase antibody per kilogram of food.

14. The composition of claim 13 wherein said anti-lipase antibody is an avian anti-lipase antibody.

* * * * *